United States Patent [19]

Treharne

[11] Patent Number: 4,776,329

[45] Date of Patent: Oct. 11, 1988

[54] RESORBABLE COMPRESSING SCREW AND METHOD

[75] Inventor: Richard Treharne, Memphis, Tenn.

[73] Assignee: Richards Medical Company, Memphis, Tenn.

[21] Appl. No.: 778,232

[22] Filed: Sep. 20, 1985

[51] Int. Cl.⁴ .............................................. A61F 5/04
[52] U.S. Cl. ........................... 128/92 YR; 128/92 YV
[58] Field of Search ............ 128/92 B, 92 BA, 92 BB, 128/92 C, 92 CA, 92 D, 92 G, 92 YV, 92 Y, 92 YR, 92 YF; 623/16

[56] References Cited

U.S. PATENT DOCUMENTS

| | | | |
|---|---|---|---|
| 3,463,158 | 8/1969 | Schmitt et al. | 628/92 BC |
| 4,338,926 | 7/1982 | Kummer et al. | |
| 4,550,449 | 11/1985 | Tunc | 623/16 |
| 4,612,923 | 9/1986 | Kronenthal | 178/92 YR |

FOREIGN PATENT DOCUMENTS

| | | | |
|---|---|---|---|
| 2947985 | 9/1981 | Fed. Rep. of Germany | 128/92 D |
| 197804 | 4/1978 | U.S.S.R. | 128/92 BB |

*Primary Examiner*—Richard J. Apley
*Assistant Examiner*—David J. Isabella
*Attorney, Agent, or Firm*—Pravel, Gambrell, Hewitt, Kimball & Krieger

[57] ABSTRACT

A method for repairing a bone fracture with a compression screw assembly is provided. First and second non-resorbable compression members are positioned so that the head portion of the compression screw can protrude from the surface of the second non-resorbable compression member after further compression is effected by the normal healing process. At least the head portion of the screw is formed of a material that resorbs upon contact with body fluids.

11 Claims, 1 Drawing Sheet

RESORBABLE COMPRESSING SCREW AND METHOD

FIELD OF THE INVENTION

This invention relates to a method and apparatus for compressing bone fractures and, more specifically, to an improvement in screw-type compression devices and procedures.

BACKGROUND OF THE INVENTION

Screw-type compression devices for compressing bone fractures have been used for years and are well known to persons skilled in the arts of orthopedic surgery and designing and manufacturing orthopedic surgical equipment. In fact, screw-type compression devices, commonly called compression hip screws, have remained virtually unchanged for many years. These devices have proven to be useful in providing necessary fixation of bone sections in fractured hips so that they can heal properly. These devices are normally left in place after the fracture has healed.

In the design of conventional screw-type compression devices, the head of the compressing screw is located at the outer surface of the device. This configuration works well as long as the head of the compressing screw remains in a fixed position relative to the outer surface of the device. However, the head of the compressing screw normally slides away from the surface of the device as a normal result of healing. This movement of the compressing screw is a desirable element of conventional devices since an otherwise fixed device would retard the normal healing process. However, full sliding movement of the compressing screw has a tendency to irritate surrounding soft tissue in some patients.

This problem is considered to be a minor nuisance that is handled several ways. The compressing screw is surgically retightened or the end of the compressing screw is covered by a substance such as bone cement. Alternatively, the compressing screw can be surgically removed. Another solution is to remove the compressing screw immediately after the screw is tightened in order to avoid another surgical procedure. However, this latter solution generally requires that the patient be handled with extreme care following surgery to prevent the separation of the fracture until the bone fragments are adequately rejoined. If successful, the problem of soft tissue irritation is avoided. In summary, the current state of the art gives the surgeon a dilemma: he can leave the compression screw in and risk soft tissue irritation or he can take the screw out and risk disassembly of the fracture.

The purpose of this invention is to provide a solution to the above-described problem of soft tissue irritation during the use of screw-type compression devices, without requiring an additional surgical procedure or expose the patient to the risk of post-op fracture separation.

SUMMARY OF THE INVENTION

The invention relates to an apparatus and a method for eliminating soft tissue irritation caused by the movement of compressing screws used in conventional screw-type compression devices for orthopedic surgery, especially of the hip. The apparatus and method include the use of a compressing screw formed of a resorbable material to either totally replace the conventional metallic screws or replace the metallic screws after the metallic screws are used to compress the fracture. The resorbable compressing screws can prevent separation of the fracture until after normal healing has significantly reduced the danger of separation and without later causing soft tissue irritation.

BRIEF DESCRIPTION OF THE DRAWINGS

A detailed description of an exemplary embodiment of the invention is set forth below, which, when taken with the following drawings, will provide a better understanding of the invention.

DETAILED DESCRIPTION OF AN EXEMPLARY EMBODIMENT

Figure 1:
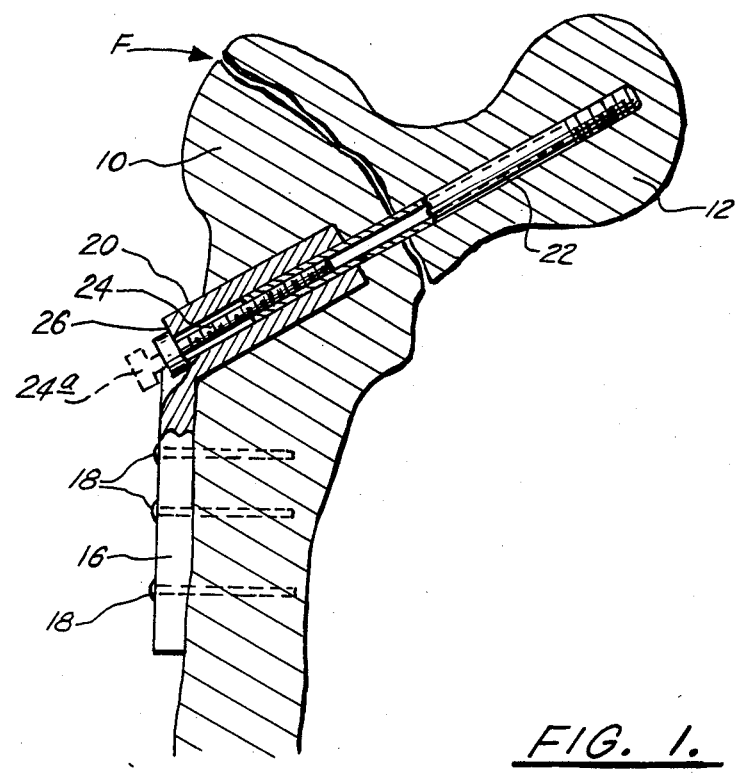
FIG. 1 is a sectional schematic view of a conventional screw-type compression device for compressing a fracture in a femur, with the broken lines showing the screw protruding after the fracture has undergone further compression during healing.

Referring to the drawings, FIG. 1 illustrates a fracture F between bone sections 10, 12 in a femoral head, which have been compressed by a conventional screw-type compression device. The compression device includes a hip screw plate 16 that is joined to the femur by bone screws 18 and a barrel section 20 that is inserted into an opening surgically formed in the bone section 10. A lag screw 22 is threaded into the bone section 12, the lag screw 22 moving freely within the barrel 20.

In order to compress the bone sections 10, 12, a compressing screw 24 is threaded into the outer end of the lag screw 22 and tightened until the head of the screw 24 contacts an outer edge 26 of the barrel 20. Further tightening of the compressing screw 24 pulls the lag screw 22 a greater distance into the barrel 20 and operates to compress the fracture F. At this point, the compressing screw prevents the fracture F from separating, but does not prevent further compression due to the normal healing process of the bone.

The broken lines identified by reference numeral 24a illustrate the position of the compressing screw 24 after further compression by the normal healing process, which causes the lag screw 22 to slide farther into the barrel 20 resulting in the head of the compressing screw 24 protruding from the surface of the hip screw 16. This problem is solved in accordance with the present invention by replacing the normally metallic compressing screw 24 with a compressing screw manufactured from a material that resorbs, that is, a screw that dissolves at a predetermined rate after it comes in contact with body fluids.

In one embodiment, the resorbable screw is formed with sufficient strength to replace the metallic compressing screw. Alternatively, the fracture would be compressed with a metallic compressing screw that is then replaced by a resorbable screw having sufficient strength 20 to hold the fracture and resorb over time as the outer end moves away from the edge 26.

Resorbable materials which have been found to be suitable for devices such as the compressing screw 24 include poly(DL-lactide) and a copolymer of glycolide and DL-lactide known as poly(DL-lactide-co-glycolide). These materials and methods for forming them are described in detail in U.S. patent application Ser. No. 610,965, filed May 16, 1984 entitled BIODEGRAD- ABLE PROSTHETIC DEVICE, which is owned by the same entity that owns the instant invention. The subject matter of the referenced application is incorporated herein by reference as though fully set forth. As described below a preferred material is poly(DL-lactide) with a weight molecular weight of 40,000-160,000 (+20,000) and having a chemical formula $(C_6H_8O_5)_n$ and the following chemical composition:

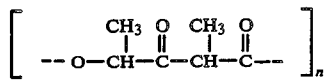

Compression screws are formed of poly(DL-lactide) (DL-PLA), poly(DL-lactide-co-glycolide) (DL-PLG) at a 60:40 respective mole ratio of lactide to glycolide, and poly(L-lactide) (L-PLA) by injection molding. Quantities of each of the above mentioned biodegradable polymers charged Quantities of each of the above mentioned biodegradable polymers were charged into the hopper of screw-plunger-type injection molder, calendered through the barrel of the molder until it reached a predetermined processing temperature, and injected under pressure into a mold tooled to the shape of a screw. A removable metal insert was used to form a hexagonal socket in the head of formed screws. After solidification, formed screws were removed from the mold. Screws formed of DL-PLA and 60:40 DL-PLG were processed at temperatures of 138° C. and 113° C., respectively. Screws were also formed from L-PLA using the same method but at 180° C. The formed screws had a threaded shaft 2.5 centimeter long and 0.55 centimeters in diameter with 12.6 threads per centimeter.

Tensile and torsional tests were performed on screws formed from DL-PLA and 60:40 DL-PLG. The screws made from L-PLA did not haee enough structural integrity to test. The tensile strength of formed screws was determined by measuring the force required to cause the screw to break when gripped from the head of the screw and a pair of nuts threaded onto the opposite end of the screws. Torsional tests were performed to determine the maximum torque required to cause a hexagonal wrench to slip within the hexagonal socket molded into the head of the screw (denoted as wrench failure), the torque required to cause the head of formed screws to shear away from the shaft of formed screws (denoted as head-shaft failure), and the torque required to cause the shaft of formed screws to shear away when a rotational force was applied to the shaft only (denoted as shaft failure). The average test results are shown in the following table:

| RESULTS OF MECHANICAL TESTING OF DL-PLA AND 60:40 DL-PLG SCREWS | | | | |
|---|---|---|---|---|
| Failure Material | Tensile Strength, lb. | Wrench Failure, in-lb. | Head-shaft Failure in-lb. | Shaft Failure in-lb. |
| DL-PLA | 144 | 4.3 | 9.3 | 8.6 |
| 60:40 DL-PLG | 63 | 0.5 | 1.5 | 0.7 |

As shown, the poly(DL-lactide) screws exhibited greater tensile and torsional strength and it was selected as the preferable material from which to form biodegradable compressing screws.

As with all resorbable materials, the degradation rate should be adjusted so that the portion of the screw exposed to body fluids would degrade after it is not needed to hold the fracture together. It has been found that a fracture in the femur compresses sufficiently well enough after two days that the screw is no longer necessary. However, for most resorbable materials, strength must be balanced against absorption time, keeping in mind that in general the stronger the screw the longer the absorption time. Depending on the size and shape of the compressing screw and its chemical makeup, a targeted absorption rate of 30 days is believed to be sufficient to maintain the structural integrity of the screw for at least the critical two day post-op healing period.

The degradation or absorption of screws can be regulated by adjusting the chemical composition of the resorbable material and/or by irradiation techniques, in a known way.

In order to adjust the degradation rate of compressing screws formed of the biocompatible material described above, various methods can be used. The poly (DL-lactide) material from which the preferable compressing screw is formed should have a molecular weight of about 40,000-120,000. That material can be exposed to gamma radiation ranging from 2.5 MRAD to about 5.0 MRAD, depending on the degradation rate that is desired, chemical makeup of the device, and configuration of the device. This procedure will be within the scope of one with ordinary skill in the art to determine optimum exposure time and the optimum degradation rates and procedures for providing them.

The resulting molecular weight upon degradation may be calculated according to standard viscosity and gel permeation chromotography tests. As a general guide, 2.5 Mrads results in approximately a 25% reduction in molecular weight of the polymer, while radiation on the order of 4.5 to 5.0 Mrad results in approximately a 50% reduction of molecular weight of the polymer. Gamma radiation on the order of 1.5 to 2.5 Mrad results in a sterilization of the polymer.

Irradiation as described can be utilized to regulate degradation rate since exposure to gamma radiation affects molecular weight and a polymer of lower molecular weight results in faster degradation in the environment than does a polymer of higher molecular weight. Since a polymer of higher molecular weight is easier to fabricate, the irradiation process may be used to reduce the molecular weight of an already fabricated higher molecular weight polymer in order to effectuate faster degradation. By this means, the molecular weight and absorption time of the polymer may be adjusted by irradiation.

The subject compressing screw can be made entirely of a material of a particular molecular weight and then irradiated in order to reduce that molecular weight and increase degradation. For example, a portion of the screw 24 such as the head may be formed with a molecular weight lower than that of the remainder of the screw. Since the lower molecular weight material would undergo faster degradation, the head would dissolve faster and not result in irritation to surrounding tissue as the fracture F compresses upon healing, causing the compressing screw 24 to back away from the surface 26.

Alternatively, the head could be formed of resorbable material and the threaded portion of metal so that only the head would absorb in body fluids, with a mechanical interlock between the two sections.

Figure 2:
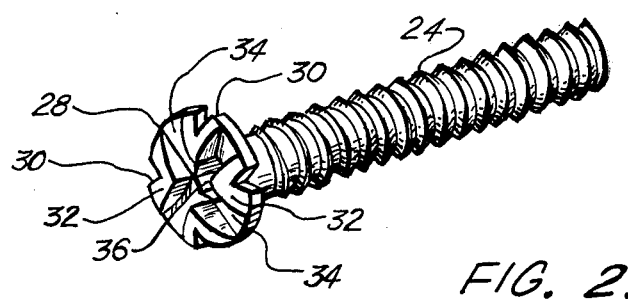
FIG. 2 is a perspective view of a compressing hip screw showing an alternate shape to accelerate the degradation rate.

As shown in FIG. 2, the screw 24 can also be provided with a head 28 with a configuration designed to allow a faster absorption rate by exposing more of the surface area to surrounding body fluids. Instead of a normally rounded head, the screw 24 can include a head 28 with notches 30 in the elevated portions 32 that define slots 34 that accommodate a driver (not shown) and/or an opening 36 in the center of the slots 34. Other configurations for exposing a greater portion of the head 28 to body fluids could also be used such as having a cannulated screw.

Thus, a compressing screw formed of a material that absorbs on contact with body fluids is provided that eliminates the disadvantages of an all-metal bone plate. It is contemplated that the invention described in the foregoing detailed description may be modified or improved upon without departing from the spirit of the invention, and that all such modifications and variations be within the scope of the appended claims.

What is claimed is:

1. A method for repairing a bone fracture with a compressing screw having a head portion and first and second non-resorbable compression members positioned so that the head portion of the screw can protrude from the surface of the second non-resorbable compression member after further compression is effected by the normal healing process, comprising the steps of:
   (a) connecting the first non-resorbable compression member to a first bone section on one side of a fracture;
   (b) connecting the second non-resorbable compression member to a second bone section on the other side of the fracture, the first and second members cooperating in such a way that the compressing screw can be used to compress the fracture by pulling the holding the first and second members together; and
   (c) compressing the fracture by utilizing the compressing screw with the head portion spaced from the bone fracture area and that bears against the first non-resorbable compression member, at least the head portion being formed of a material that resorbs on contact with body fluids.

2. The method of claim 1, wherein the head is formed with an opening of the middle thereof to expose a greater portion of the head to body fluids.

3. The method of claim 1, wherein the head is formed with notches to expose a greater portion of the head to body fluids.

4. The method of claim 2, wherein the resorbable material is formed of poly (DL-lactide) having a weight molecular weight of 40,000-160,000.

5. A method for repairing bone fractures with a compressing screw having a head portion, and first and second non-resorbable compression members positioned so that the head portion of the screw can protrude from the surface of the second non-resorbable compression member after further compression is effected by the normal healing process, comprising the steps of:
   (a) connecting the first compression member to a first bone section on one side of a fracture;
   (b) connecting the second compression member to a second bone section on the other side of the fracture, the first and second members cooperating in such a way that a compressing screw can be used to compress the fracture by pulling the first and second members together,
   (c) compressing the fracture by inserting and tightening a non-resorbable compressing screw, and
   (d) replacing said non-resorbable compressing screw with a compressing screw with at least head portion formed of a material that resorbs on contact with body fluids, after the non-resorbable screw has been used to compress the fracture.

6. The method of claim 5, wherein the compressing screw is formed entirely of resorbable material.

7. The method of claim 6, wherein the head is formed of a material that resorbs faster than the remainder of the screw.

8. The method of claim 5, wherein the head is formed with an opening on the middle thereof to expose a greater portion of the head to body fluids.

9. The method of claim 5, wherein the head is formed with notches to expose a greater portion of the head to body fluids.

10. The method of claim 6, wherein the resorbable material is formed of poly(DL-lactide) having a weight molecular weight of 40,000-160,000.

11. A method for repairing bone fractures with a compressing screw having a head portion and first and second non-resorbable compression members positioned so that the head portion of the screw can protrude from the surface of the second non-resorbable compression member after further compression is effected by the normal healing process, comprising the steps of:
   (a) connecting the first compression member to a first bone section on one side of a fracture;
   (b) connecting the second compression member to a second bone section on the other side of the fracture, the first and second members cooperating in such a way that the compressing screw can be used to compress the fracture by pulling and holding the first and second members together, and
   (c) compressing the fracture by utilizing a compressing screw formed entirely of resorbable material with a head portion that resorbs faster than the remainder of the screw.

* * * * *